United States Patent
Steinlin et al.

(10) Patent No.: US 11,691,876 B2
(45) Date of Patent: Jul. 4, 2023

(54) OZONE GENERATING MACHINE WITH ELECTRICAL CLOSED CABINET COOLED BY CLOSED LOOP

(71) Applicant: SUEZ GROUPE, Paris la Defense (FR)

(72) Inventors: Bruno Steinlin, New Jersey, NJ (US); Tito Scherrer, Rueschlikon (CH); Luca Ramoino, Uster (CH)

(73) Assignee: SUEZ GROUPE, Paris (FR)

( * ) Notice: Subject to any disclaimer, the term of this patent is extended or adjusted under 35 U.S.C. 154(b) by 672 days.

(21) Appl. No.: 16/622,927

(22) PCT Filed: Jun. 29, 2018

(86) PCT No.: PCT/EP2018/067521
§ 371 (c)(1),
(2) Date: Dec. 16, 2019

(87) PCT Pub. No.: WO2019/002531
PCT Pub. Date: Jan. 3, 2019

(65) Prior Publication Data
US 2020/0156941 A1 May 21, 2020

(30) Foreign Application Priority Data
Jun. 30, 2017 (EP) .................................. 17305839

(51) Int. Cl.
*C01B 13/11* (2006.01)
*A61L 2/20* (2006.01)
(Continued)

(52) U.S. Cl.
CPC ............ *C01B 13/115* (2013.01); *A61L 2/202* (2013.01); *B63J 2/02* (2013.01); *C02F 1/4672* (2013.01);
(Continued)

(58) Field of Classification Search
CPC ............... C01B 13/115; C01B 2201/74; C01B 2201/90; A61L 2/202; B63J 2/02;
(Continued)

(56) References Cited

U.S. PATENT DOCUMENTS

2015/0291459 A1* 10/2015 Choi ........................ B63J 4/002
261/34.1

FOREIGN PATENT DOCUMENTS

EP 1882674 A1 1/2008
WO 2008039147 A2 4/2008

OTHER PUBLICATIONS

Database WPISection CH, Week 2015223 Dec. 2014 (Dec. 3, 2014); Thompson Scientific, London, GB, Class E36, AN 2015-07862XXP002776657, & CN 104 176 710 A (HAN C)Dec. 3, 2014 (Dec. 3, 2014) abstract; International Search Report; Application No. PCT/EP2018?067521 completed Sep. 5, 2018.
(Continued)

*Primary Examiner* — Xiuyu Tai
(74) *Attorney, Agent, or Firm* — Landmark Intellectual Property Law, PLLC; Gregory Murphy

(57) ABSTRACT

Ozone generating machine (OGM) for generating ozone in a ship, comprising:
an ozone generator with at least two electrodes separated by an ozonizing gap and at least a gas inlet for receiving a feed gas containing dioxygen, and a gas outlet for exhausting gas comprising ozone to an ozone circuit of the ship,
a main liquid cooling circuit (CWP, CWT), with at least a cooling portion in the ozone generator, to be connected with a cooling circuit of a ship,
a liquid-liquid heat exchanger (LLHEX) connected with the main liquid cooling circuit (CWP, CWT), and
an electrical closed cabinet (ECB) comprising an electric current converter (ECV),
(Continued)

characterized in that the ozone generating machine (OGM) further comprises a closed loop cooling liquid circuit (CLC) comprising a converter liquid cooling portion (CECV) arranged to cool the electric current converter (ECV) and connected with the liquid-liquid heat exchanger (LLHEX).

15 Claims, 3 Drawing Sheets

(51) Int. Cl.
  *B63J 2/02* (2006.01)
  *C02F 1/467* (2023.01)
  *C02F 103/00* (2006.01)
(52) U.S. Cl.
  CPC ...... *C01B 2201/74* (2013.01); *C01B 2201/90* (2013.01); *C02F 2103/008* (2013.01); *C02F 2201/001* (2013.01); *C02F 2201/782* (2013.01)
(58) Field of Classification Search
  CPC ... B63J 4/002; C02F 1/4672; C02F 2103/008; C02F 2201/001; C02F 2201/782; C02F 2307/00; C02F 2103/08; C02F 2303/04; C02F 1/78; B01F 25/313; B01F 23/23121; B01F 23/21322; B01F 23/2323; B01F 23/23; B01F 23/237613; B01F 2101/305; B63B 13/00
  See application file for complete search history.

(56) References Cited

OTHER PUBLICATIONS

Database WPISection Ch, Week 2017295 Apr. 2014 (Apr. 5, 2017)Thompson Scientific, London, GB; Class E36, AN 2017-24153EXP002776659, & CN 206 069 368 U (Beijing Jindawanxiang Enviornmental Prot)Apr. 5, 2017 (Apr. 5, 2017) abstract; International Search Report for International Application No. PCT/EP2018/067521 completed Sep. 5, 2018.
Database WPISection EI, Week 20115513 Jul. 2011 (Jul. 13, 2011)Thompson Scientific, London, GB, Class V04, AN 2011-k23216 XP002776658, & CN 201 898 690 U (Jiangsu Kanger Ozone Co Ltd) Jul. 13, 2011 (Jul. 13, 2011) cited in the application the whole document; International Search Report for International Application No. PCT/EP2018/067521 completed Sep. 5, 2018.

\* cited by examiner

OZONE GENERATING MACHINE WITH ELECTRICAL CLOSED CABINET COOLED BY CLOSED LOOP

The present invention relates to the field of water treatment in ship thanks to ozone, and relates in particular to an ozone generating machine equipped with an electrical closed cabinet.

It is known from the prior art document CN201898690 an electrical cabinet for an ozone generator that is cooled by air, using the physical behavior of hot air to flow upward and cold air to flow downward.

The disadvantages of the electrical cabinet disclosed by this document is that cooling efficiency is poor and cooling repartition is not dedicated to electrical components or devices and therefore not sufficient for high demanding cooling electrical components installed in the electrical cabinet. Thereby lifetime of electrical components can decrease and safety is not ensured is case of failure. In addition, in severe environments such as in a ship, it might be required that the electric cabinet satisfy a given degree of protection against intrusion (dust, water), while being installed in a hot environment (up to 55° C.), complicating the cooling of the internal components.

An aim of the present invention is to overcome the disadvantages of the prior art document mentioned above, and in particular to propose an ozone generating machine comprising an electrical closed cabinet with high cooling capacities, high efficiency repartition of the cooling and high safety level.

A first aspect of the present invention is an zone generating machine for generating ozone in a ship, comprising:
  an ozone generator with at least two electrodes separated by an ozonizing gap and a dielectric layer, the ozone generator comprising at least a gas inlet for receiving a feed gas containing dioxygen, and a gas outlet for exhausting gas comprising ozone to an ozone circuit of the ship.
  a main liquid cooling circuit, at least one portion of the main liquid cooling circuit being located inside the ozone generator, to be connected with a cooling circuit of the ship,
  a liquid-liquid heat exchanger connected with the main liquid cooling circuit, and
  an electrical closed cabinet comprising an electric current converter,
characterized in that the ozone generating machine further comprises a closed loop cooling liquid circuit connected with the liquid-liquid heat exchanger and comprising a converter liquid cooling portion arranged to cool the electric current converter.

This allows to propose an ozone generating machine with a high cooling efficiency, dedicated to a high demanding cooling electrical component and fitted to its need, providing a high safety level due to high cooling capacity and also due to the closed loop arrangement of the cooling liquid circuit. Indeed, in case of failure occurring in the liquid circuit, only the small volume of the closed loop can flow inside the electrical closed cabinet but not the high volume of the main liquid cooling circuit nor the cooling circuit of the ship. That is to say, as the electrical closed cabinet is closed to avoid dust and any other disturbances like moisture or the like to enter into the electrical closed cabinet, a liquid leakage can damage electrical components installed inside said electrical closed cabinet such as electric current converter or any other electrical component or annex components inside electrical closed cabinet. Thereby, as the closed loop is hydraulically disconnected/distinct from the main liquid cooling circuit due to the liquid-liquid heat exchanger, such risk is highly reduced.

Advantageously, the liquid-liquid heat exchanger comprises at least two internal circuits, one internal circuit being connected to the main liquid cooling circuit, and one other internal circuit being connected to the closed loop cooling liquid circuit.

Advantageously, the liquid-liquid heat exchanger is installed in a narrow area outside the electrical closed cabinet.

This allows to structurally disconnect the two hydraulic circuits, that is to say there is no exchange of liquid between the main liquid cooling circuit and the closed loop cooling liquid circuit. The thermal connection is made by the liquid-liquid heat exchanger, allowing a high cooling efficiency of the electrical closed cabinet and the electric current converter. The location of the liquid-liquid heat exchanger allows to avoid any leakage of the liquid-liquid heat exchanger inside the electrical closed cabinet. The liquid-liquid heat exchanger is not necessarily placed in the ozone generator.

Advantageously, the closed loop cooling liquid circuit has a total volume smaller than five liters, and more preferably smaller than three liters.

This limited volume of the closed loop cooling liquid circuit, reduces the risk of contact between the liquid and any electrical or electronical component in case of leakage inside the electrical closed cabinet or failure with the electrical components of the electrical closed cabinet.

Advantageously, a lowest electrical device of the electrical closed cabinet is installed at a predetermined distance from an internal lowest surface of the electrical closed cabinet, thereby defining an electrical closed cabinet bottom volume where there is no electrical device, and the closed loop cooling liquid circuit has a total volume not greater than said electrical closed cabinet bottom volume, in order to avoid a contact between lower electrical device and closed loop cooling liquid in case of liquid leakage of said closed loop cooling liquid circuit.

Advantageously, the predetermined distance is 8 cm.
Advantageously, the predetermined distance is 16 cm.
Advantageously, the electrical closed cabinet is equipped with a liquid check valve arranged in a bottom area of the electrical closed cabinet to evacuate liquid from the electrical closed cabinet and to block air to enter inside the electrical closed cabinet.

This allows to propose an electrical closed cabinet with high safety requirements, permitting the provision of the bottom area which will be free from liquid in case of failure or leakage of the closed loop cooling liquid circuit. That is to say that liquid level in case of leakage will never reach the level of the lowest electrical device, thereby reinforcing electrical safety and lifetime.

This allows to evacuate liquid in case of liquid failure with an airproof check valve to avoid any dust to enter inside the electrical closed cabinet and to evacuate liquid is case of failure.

The predetermined distance is defined to ensure that there is a liquid free area at the bottom of the electrical closed cabinet. As an advantageous example, the electrical cabinet as a dimension of one meter depth, one meter width and two meters height. The predetermined distance thereby defining the electrical closed cabinet bottom volume is enough to contain all the liquid of the closed loop cooling liquid circuit, ensuring high safety margins.

Advantageously, the electrical closed cabinet further comprises an air-liquid heat exchanger connected with the closed loop cooling liquid circuit and arranged to cool air inside the electrical closed cabinet.

This allows to cool the air inside the electrical closed cabinet with high efficiency.

Advantageously, the air-liquid heat exchanger comprises an internal circuit connected to the closed loop cooling liquid circuit.

This allows to benefit from the cooling capacity and safety level of the closed loop liquid circuit, thereby ensuring high cooling efficiency.

Advantageously, the electrical closed cabinet further comprises an electric current transformer and a transformer fan arranged to blow air onto said electric current transformer, after sucking it from the said air-liquid heat exchanger.

This allows to propose an electrical closed cabinet with electric current transformer, thereby increasing electric capacity of the electrical closed cabinet to provide ozone generating machine with adequate current characteristics. The necessary cooling of the electric current transformer is ensured by the transformer fan, rendered highly efficient thanks to the air-liquid heat exchanger.

Advantageously, the ozone generating machine further comprises a heat exchanger fan arranged to suck air from said air-liquid heat exchanger.

This allows to enlarge the cooling capacity of the air-liquid heat exchanger, so that necessary cooling is done in an efficient manner.

Advantageously, the ozone generating machine further comprises a cabinet fan arranged to create an air circulation inside said electrical closed cabinet.

This allows to propose a high efficient circulation of air inside the electrical closed cabinet.

Advantageously the ozone generating machine further comprises at least one air temperature sensor arranged to measure air temperature inside said electrical closed cabinet.

This allows to monitor air temperature inside the electrical closed cabinet and to better control the temperature, by acting on the temperature of the closed loop cooling liquid circuit for example.

Advantageously, the ozone generating machine further comprises at least one liquid temperature sensor arranged to measure liquid temperature inside the closed loop cooling liquid circuit.

This allows to monitor liquid temperature inside the electrical closed cabinet and to better control the temperature, by acting on the temperature of the closed loop cooling liquid circuit for example.

Advantageously, the ozone generating machine further comprises:
- at least one liquid temperature sensor arranged to measure a liquid temperature inside the closed loop cooling liquid circuit and arranged upstream the electric current converter,
- at least one flow switch arranged to detect liquid flow inside the closed loop cooling liquid circuit, in order to monitor that said electric current converter is cooled.

Advantageously, the ozone generating machine further comprises at least one liquid flow sensor arranged to measure liquid flow inside the closed loop cooling liquid circuit.

Advantageously, the ozone generating machine further comprises at least one liquid pressure sensor arranged to measure liquid pressure inside the closed loop cooling liquid circuit.

Advantageously, the ozone generating machine further comprises at least one liquid pressure indicator arranged to measure liquid pressure inside the closed loop cooling liquid circuit.

This allows to propose an ozone generating machine with an electrical closed cabinet with a highly fitted temperature management system to ensure that electric current converter is cooled enough. In particular, a loss/decrease of flow, a loss/decrease of pressure in the closed loop cooling circuit detected by the above mentioned sensors might be used to send a warning message or to switch off the ozone generating machine, as it might indicate a leakage in the circuit. Similarly, a too high temperature within the closed cabinet detected by the above mentioned temperature sensors might be used to send a warning message or to switch off the ozone generating machine, as it might indicate a loss of cooling of the system.

Advantageously, the ozone generating machine further comprises a liquid circulation pump connected to the closed loop cooling liquid circuit.

This allows to provide a circulation of the liquid inside the closed loop cooling liquid circuit, so that better cooling efficiency is reached.

A second aspect of the present invention concerns a ship comprising an ozone generating machine according to the first aspect of the present invention.

Other features and advantages of the present invention will appear more clearly from the following detailed description of particular non-limitative examples of the invention, illustrated by the appended drawings where:

Figure 1:
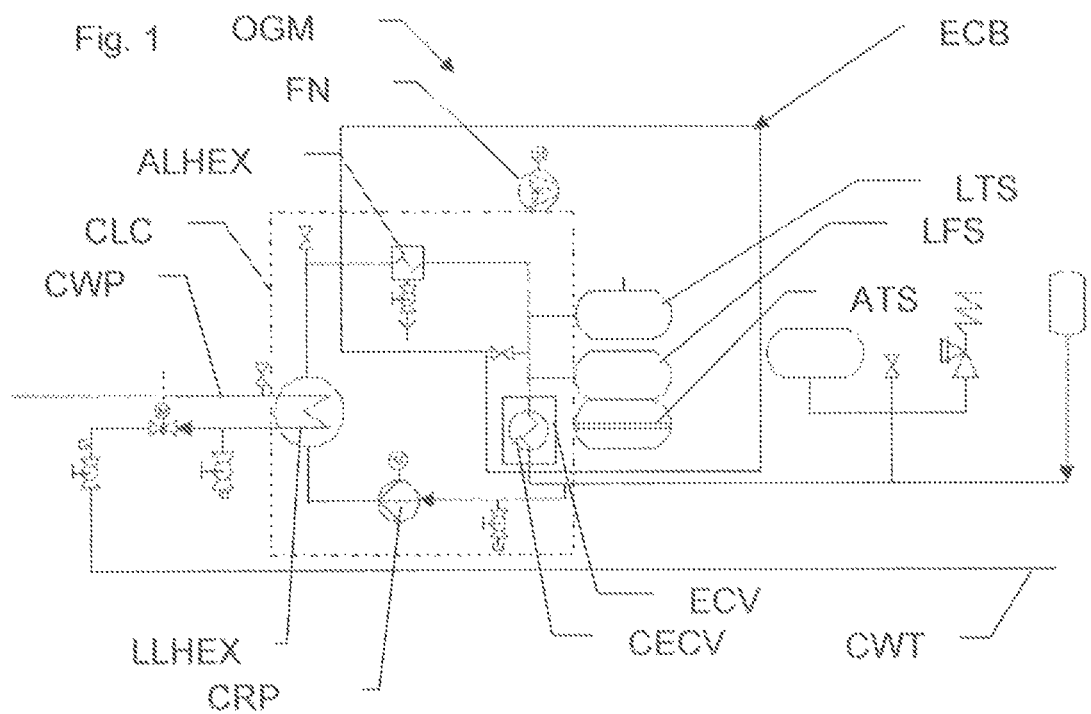
FIG. 1 represents a schematic diagram of a part of the ozone generating machine comprising an electric closed cabinet according to the invention.
Figure 2:
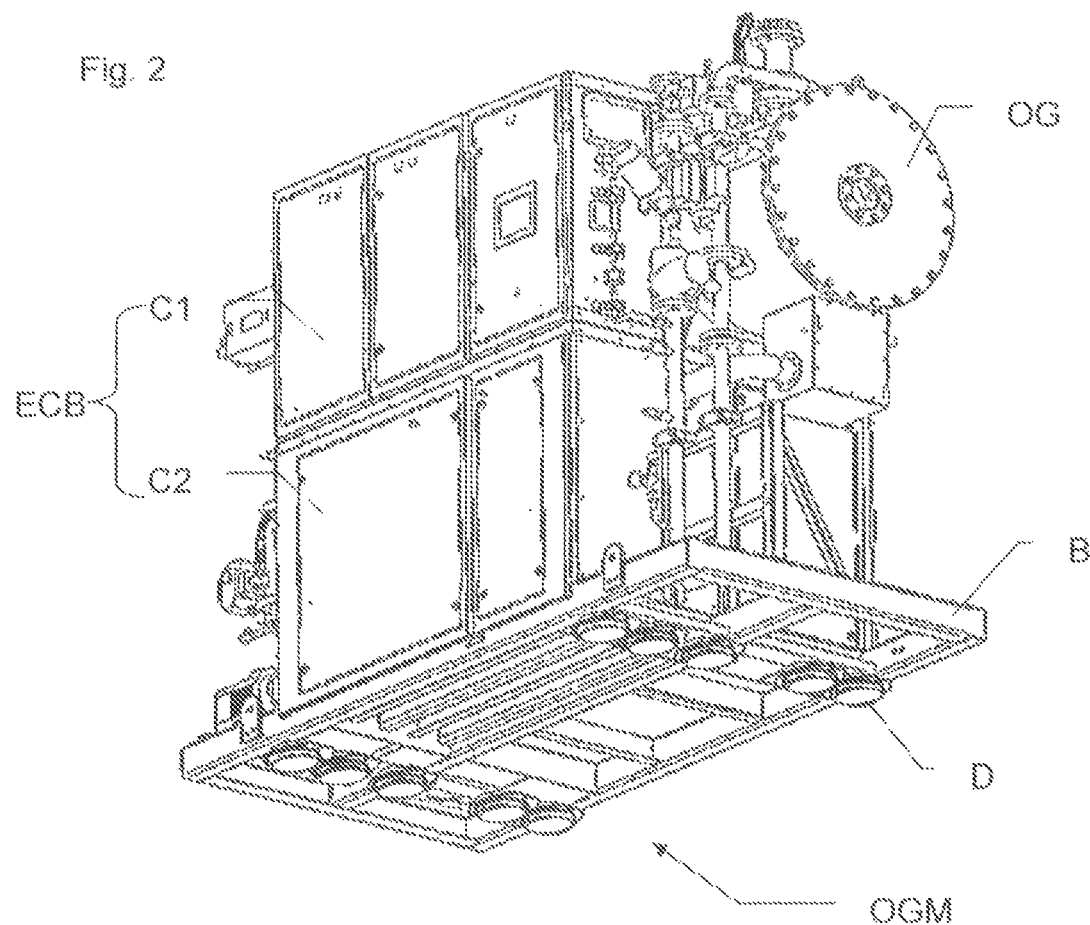
FIG. 2 represents a perspective view of the ozone generating machine according to the present invention.
Figure 3:
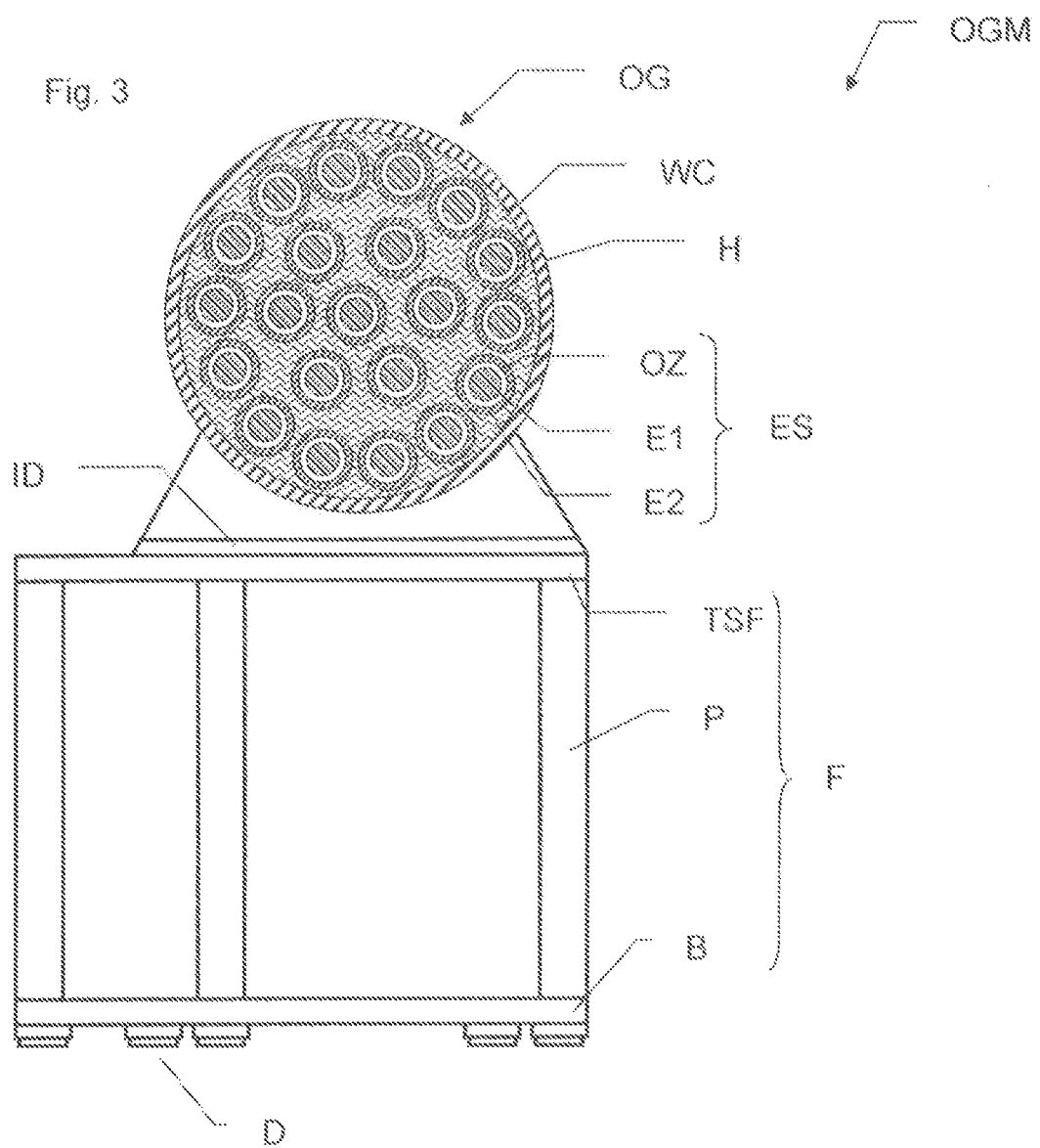
FIG. 3 represents a simplified cross section of the ozone generator according to the present invention.
Figure 5:
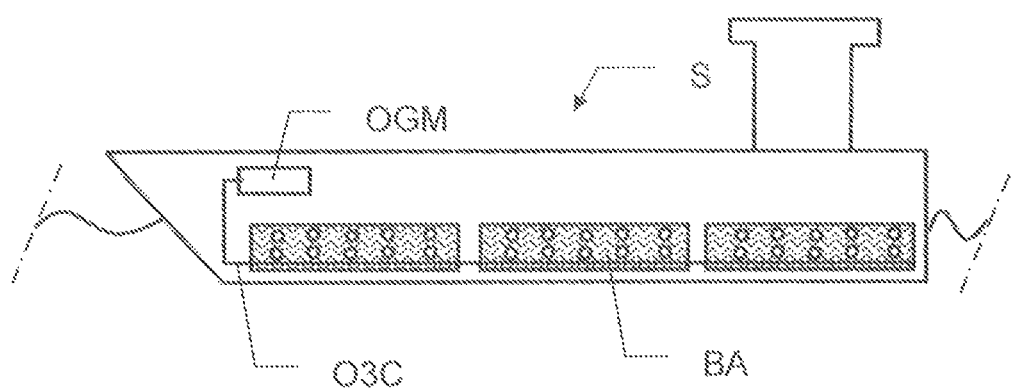
FIG. 5 represents a ship equipped with an ozone generating machine according to the invention.

The ozone generating machine OGM machine shown on FIGS. 1, 2 and 3 mainly comprises an ozone generator OG, an electrical closed cabinet ECB, which can be done also in two separated or half cabinets C1 and C2, and a frame F for supporting the ozone generator OG and the electrical closed cabinet ECB. Of course, such machine comprises also numerous valves, sensors, pipes, electric devices to ensure automatic generation of ozone. In particular, the depicted machine is designed for use in ships or vessels, having a need to sanitize ballasts water, to avoid cross-harbor water contamination for example. FIG. 5 represents a ship S comprising ballasts BA (full of water) and an ozone generating machine OGM, connected to an ozone circuit O3C of the ship S, to supply ozone to the ballasts BA. Indeed, water contained in the ballasts BA need to be treated/sanitized before being released, and ozone is supplied by the ozone circuit O3C directly into the ballasts BA, where ozone bubbles are visible.

The ozone generator OG comprises a plurality of electrodes sets ES placed within a housing H, as shown on FIG. 3. Each electrodes set comprises two electrodes E1 and E2, separated by an ozonizing gap OZ, and a dielectric layer (not shown on figures for clarity). The ozone generating machine OGM comprises also an electric power unit EPU shown FIG. 4 for supplying electric current to each of the electrodes sets ES. Each ozonizing gap OZ is connected upstream to a gas inlet O2IN of the ozone generator OG for receiving a gas containing dioxygen, and downstream to a gas outlet O3OUT for exhausting gas containing ozone, when the ozone generating machine OGM is operated.

In an embodiment, the electrodes are metallic, and the dielectric layer comprises a ceramic coating, applied onto at least one of the electrodes.

The gas containing dioxygen might be supplied by the ship network, a bottle, or might be air. When electric power is supplied to the electrodes and gas flow is established, electric discharges occur in the ozonizing gap OZ between the electrodes E1 and E2 allowing corona affect, and a portion of oxygen supplied at the gas inlet O2IN is transformed into ozone, which is exhausted at the gas outlet O3OUT in a given amount.

Figure 4:
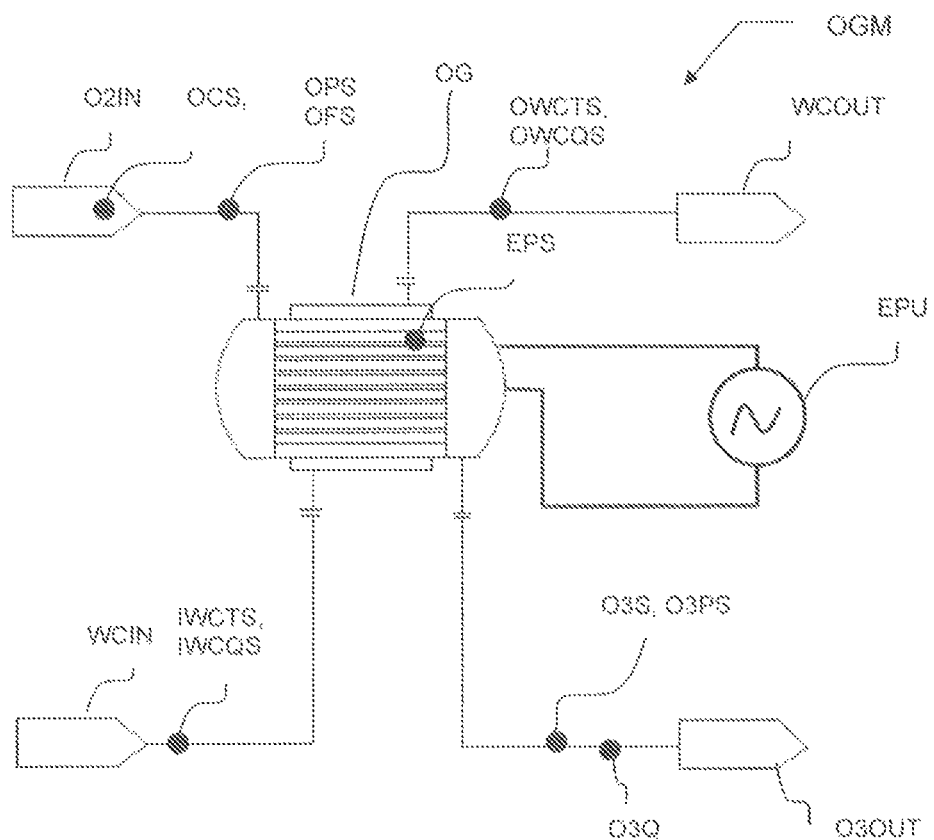
FIG. 4 represents a schematic diagram of the ozone generating machine according to the present invention.

To ensure stable conditions during production of ozone, a liquid cooling circuit comprises a cooling path within the ozone generator OG, so that a cooling liquid can flow through the ozone generator OG, to cool directly each of the electrodes sets ES. FIG. 3 shows that cooling water WC is present in the housing H of ozone generator OG. The ozone generator OG comprises an inlet of water cooling WCIN, and an outlet of water cooling WCOUT as shown in FIG. 4. As shown in FIG. 1, the ozone generating machine OGM further comprises a main liquid cooling circuit CWP. CWT, and at least one portion of the main liquid cooling circuit CWP, CWT being located inside the ozone generator OG, to be connected with a cooling circuit of the ship, and further comprises a liquid-liquid heat exchanger LLHEX connected with the main liquid cooling circuit CWP, CWT. Further, the main liquid cooling circuit CWP, CWT comprises an upstream portion CWP, located upstream the liquid-liquid heat exchanger LLHEX and a downstream portion located downstream the liquid-liquid heat exchanger LLHEX. The liquid-liquid heat exchanger LLHEX is located outside and narrow the electrical closed cabinet ECB. The at least one portion of main liquid cooling circuit CWP, CWT being located inside the ozone generating machine OGM is thereby connected to the inlet of water cooling WCIN, and to the outlet of water cooling WCOUT, as being part of the main liquid cooling circuit CWP, CWT, considering FIGS. 1 and 4 together.

As shown in FIG. 1, the electrical closed cabinet ECB comprises an electric current converter ECV distributing current to the electrodes sets ES of the ozone generator OG. To provide an efficient cooling of the electric current converter ECV, the ozone generating machine OGM further comprises a closed loop cooling circuit liquid CLC connected with the liquid-liquid heat exchanger LLHEX and comprising a converter liquid cooling portion CECV arranged to cool the electric current converter ECV. The ozone generating machine OGM further comprises a liquid circulation pump CRP connected to the closed loop cooling liquid circuit CLC, allowing circulation of the liquid inside the closed loop cooling liquid circuit CLC. Said cooling liquid is preferably water or water with additives, but could be any other calorific transport fluid.

The liquid-liquid heat exchanger LLHEX comprises at least two internal circuits, one internal circuit being connected to the main liquid cooling circuit CWP, CWT, and one other internal circuit being connected to the closed loop cooling liquid circuit CLC. The closed loop cooling liquid circuit CLC is thereby partly arranged inside the closed electrical cabinet ECB. As the electrical closed cabinet ECB is closed to avoid any dust or the like to enter inside, and create pollution, the electrical components or devices of the electrical closed cabinet ECB should be cooled, as there is no natural fresh air convection as for open electrical cabinet. The main electrical component is the electric current converter ECV that is cooled by the converter liquid portion CECV. Other electrical components such as electric current transformer are cooled thanks to a transformer fan FN arranged to blow air onto said electric current transformer after sucking air from an air-liquid heat exchanger ALHEX of the electric closed cabinet ECB. The air-liquid heat exchanger ALHEX comprises an internal circuit connected to the closed loop cooling liquid circuit CLC. The transformer fan FN can also blow air to create air circulation inside electrical closed cabinet ECB.

A set of sensors is provided with the electrical closed cabinet ECB, such as an air temperature sensor ATS arranged to measure air temperature inside said electrical closed cabinet ECB, a liquid temperature sensor LTS arranged to measure liquid temperature inside the closed loop cooling liquid circuit CLC, a flow switch or a flow sensor LFS arranged to detect or to measure the flow of liquid inside the closed loop cooling liquid circuit CLC. The set of sensors can thereby provide information about the health of the electrical closed cabinet ECB and allow to change parameters to better cool the electrical closed cabinet ECB, such as for example adjust the flow and/or the temperature of liquid in the closed loop cooling liquid circuit CLC, change the speed of the transformer fan FN, or any other adjustment or retroacting correction to allow temperature management of the electrical closed cabinet ECB.

In addition, the dot line on the closed loop cooling liquid circuit CLC is representing an example of the arrangement of the same. The closed loop cooling liquid circuit CLC presents a limited volume, for example three liters or the like, small compared to the main liquid cooling circuit CWP, CWT. This allows to have a small amount of liquid in case of leakage or failure inside the electrical closed cabinet ECB. The electrical components of devices inside the electrical closed cabinet ECB are located at a predetermined distance such as ten cm or fifty cm or the like, thereby defining an electrical closed cabinet bottom volume in order to avoid any contact between liquid and electric component. The same is done for electric current converter ECV or electric current transformer. The closed loop cooling liquid circuit CLC is equipped with a low point valve or drain valve and other necessary connecting point, and the electrical closed cabinet ECB is equipped with a low point check valve allowing a liquid leakage to be evacuated but keeping the electrical closed cabinet ECB airtight.

Also for safety, sensors of the electric current converter ECV are equipped with a switch off function in order to switch off the electric current converter ECV if needed. Safety management and switch off order are managed through a programmable logic controller usually know as PLC.

In other hand, the ozone generating machine OGM can typically be operated in the following ranges:

range of power density: [0.1 to 10] kW per square meter of electrode range of electric current frequency: [10 to 30000] Hz upper limit of peak voltage: [2-20] kV Ozone concentration at the gas outlet: 1-16% by weight Range of absolute pressure of feed gas, [0.5 bar(a)-6.0 bar(a)]

It might be desired that Nitrogen (N2) and/or Argon (Ar) is present in the feed gas at least with a concentration of: 0.1-5% by weight, and the rest is dioxygen. Alternatively, one can supply air to the ozone generator OG.

The ozone generating machine OGM is also equipped with adequate sensors to monitor and check the ozone production, and the machine can comprise, as shown on FIG. 4 an oxygen concentration sensor OCS, an oxygen pressure sensor OPS, an oxygen flow sensor OFS, an ozone concentration sensor O3S, an ozone pressure sensor O3PS, an ozone circulation flow sensor O3Q, an inlet water cooling temperature sensor IWCTS and an outlet water cooling temperature sensor OWCTS, an inlet water cooling flow sensor IWCQS and an outlet water cooling flow sensor OWCQS, electrode power measurement means EPS with for example an electrode intensity sensor, an electrode voltage sensor, and a frequency sensor. These sensors are equipped with a deported display located inside the electrical closed cabinet ECB.

The frame F supports the ozone generator OG via a top subframe TSF, lies onto the ground via a base B and comprises pillars P between the top subframe TSF and base B. The base B is also supporting the electrical closed cabinet ECB. Same conception with pillars P and top subframe TSF can be used for supporting the electrical closed cabinet ECB upon need.

Typically the base B and top subframe TSF are metallic structures comprising welded beams and plates: to ensure adequate resting surfaces or platen areas, for attachment of the components of the ozone generating machine. Welding technique is an example of assembly, but the beams and plates might be attached together with nuts/bolts/screws, to allow easy dismantling/transportation/installation of the frame F. Indeed, as the ozone generating machine OGM is designed to be installed into a ship, one shall take into account the installation in a reduced space, with limited access. This leads to choose between welding assembly for parts having small dimensions/footprint and nuts assembly for parts having larger dimensions/footprint.

Pillars P are supporting the top subframe TSF and are attached to the base B.

As shown FIG. 2, the ozone generator OG is typically located at breast height (between 1 m and 1.6 m from ground), for maintenance reasons: to provide an easy access for the electrodes E1, E2 located within the ozone generator OG, as shown FIG. 3. This is also the case for upper half cabinet C1.

The weight and dimensions of the ozone generator OG are significant (Ø of about [300-800] mm and [800-3000] mm length, weight from 50 kg to 1500 kg), added to the weight of other organs of the ozone generating machine OGM (electric cabinets C1. C2: pipes, valves . . . ) results in stress, strain and displacements when the machine is subjected to vibrations, commonly present in a marine application.

As an example, it might be required that the electrical closed cabinet ECB or any component of the OGM has to fulfil a vibration range of 2 to 100 Hz vibration, and at the resonance frequency it is not allowed to have (as described in the D. N. V standard for certification No. 2.4 "Environmental test specification for instrumentation and automation equipment,". April 2006):

more than 1 mm displacement between 2 and 13.2 Hz and more than 6860 mm/s$^2$ acceleration between 13.2 and 100 Hz, comparing the base frame to other parts especially on top of the ozone generating machine OGM.

In order to minimize the acceleration and/or displacements when subjected to vibrations, the frame F is designed in the specific following way. Cross-brace beams are positioned in the longitudinal direction of the machine, to link pairs of pillars P located under the ozone generator OG. Consequently, the pillars P linked together by the cross-brace beams are firmly held together.

In addition, the frame F comprises reinforcing plates, and in particular top reinforcing plates attached via two bolts to the top portion of the pillars P and via two bolts to the top subframe TSF, thereby increasing the rigidity of the joint. Similarly, bottom reinforcing plates are attached via two bolts to the bottom portion of the pillars P and via two bolts to the base B, thereby increasing the rigidity of the joint.

The cross-brace beams are also attached via two bolts to the reinforcing plates, to provide a simple and robust structure.

In addition, dampers D are positioned between the ground and the base B to minimize the transmission of vibrations to the frame F. At least four dampers D are placed directly below the ozone generator OG, but as shown FIG. 2, ten dampers total are attached to the bottom face of the base B. Some of these dampers are directly attached to the ground, to prevent any relative movement between the ground and the ozone generating machine OGM (slippage, falling over . . . ).

The dampers D are chosen to have a low vertical size (less than 100 mm), and to resist to the weight of the machine. Typically, such dampers D are comprising a rubber arranged between a first attachment portion attached to the frame F, and a second attachment portion, attached to or laying onto the ground.

At least four dampers D are positioned vertically below the ozone generator OG, and intermediate dampers ID are placed between the ozone generator OG and the top subframe TSF, to minimize as much as possible the vibrations of the heaviest part (the ozone generator OG) of the ozone generating machine OGM.

In addition, one should note that the cross-brace beams are positioned parallel to the longitudinal dimension of the ozone generating machine OGM, defined by the axial direction of the ozone generator OG. Therefore organs or devices might be placed between the two pairs of cross-brace beams, and the machine comprises at least one door, for closing an opening in the frame F through which the organs or devices placed between the two pairs of cross-brace beams can be removed or inserted, for maintenance reasons. In particular, it is advantageous to position and attach in the bottom portion of the ozone generating machine OGM heavy electric devices such as current transformers or converters, to increase stability. The transverse door and its opening, arranged large enough to allow passage of these devices, avoids the need to remove the cross-brace beams.

It is of course understood that obvious improvements and/or modifications for one skilled in the art may be implemented, still being under the scope of the invention as it is defined by the appended claims.

What is claimed is:

1. An ozone generating machine (OGM) for generating ozone in a ship, comprising:
   an ozone generator (OG) with at least two electrodes (E1, E2) separated by an ozonizing gap (OZ) and a dielectric layer, the ozone generator (OG) comprising at least a gas inlet (O21N) for receiving a feed gas containing dioxygen, and a gas outlet (O3OUT) for exhausting gas comprising the generated ozone to an ozone circuit of the ship to supply the generated ozone to ballasts of water of the ship,
   a main liquid cooling circuit (CWP, CWT), at least one portion of the main liquid cooling circuit (CWP, CWT) being located inside the ozone generator (OG), to be connected with a cooling circuit of the ship, a liquid-liquid heat exchanger (LLHEX) connected with the main liquid cooling circuit (CWP, CWT), and an electrical closed cabinet (ECB) comprising an electric current converter (ECV), characterized in that the ozone generating machine (OGM) further comprises a closed loop cooling liquid circuit (CLC) connected with the liquid-liquid heat exchanger (LLHEX) and comprising a converter liquid cooling portion (CECV) arranged to cool the electric current converter (ECV).

2. The ozone generating machine (OGM) according to claim 1, wherein the liquid-liquid heat exchanger (LLHEX) comprises at least two internal circuits, one internal circuit being connected to the main liquid cooling circuit (CWP, CWT), and one other internal circuit being connected to the closed loop cooling liquid circuit (CLC).

3. The ozone generating machine (OGM) according to claim 1, wherein the closed loop cooling liquid circuit (CLC) has a total volume no greater than three liters.

4. The ozone generating machine (OGM) according to claim 1:
  wherein a lowest electrical device of the electrical closed cabinet (ECB) is installed at a predetermined distance from an internal lowest surface of the electrical closed cabinet (ECB), thereby defining an electrical closed cabinet bottom volume where there is no electrical device, and
  wherein the closed loop cooling liquid circuit (CLC) has a total volume no greater than said electrical closed cabinet bottom volume, in order to avoid a contact between lower electrical device and closed loop cooling liquid in case of liquid leakage of said closed loop cooling liquid circuit (CLC).

5. The ozone generating machine (OGM) according to claim 4, wherein the electrical closed cabinet (ECB) further comprises an air-liquid heat exchanger (ALHEX) connected with the closed loop cooling liquid circuit (CLC) and arranged to cool air inside the electrical closed cabinet (ECB).

6. The ozone generating machine (OGM) according to claim 5, wherein the air-liquid heat exchanger (ALHEX) comprises an internal circuit connected to the closed loop cooling liquid circuit (CLC).

7. The ozone generating machine (OGM) according to claim 5 wherein the electrical closed cabinet (ECB) further comprises an electric current transformer and a transformer fan (FN) arranged to blow air onto said electric current transformer, after sucking it from the said air-liquid heat exchanger (ALHEX).

8. The ozone generating machine (OGM) according to claim 5 further comprising a heat exchanger fan (FN) arranged to suck air from said air-liquid heat exchanger (ALHEX).

9. The ozone generating machine (OGM) according to claim 5 further comprising a cabinet fan (FN) arranged to create an air circulation inside said electrical closed cabinet (ECB).

10. The ozone generating machine (OGM) according to claim 1, further comprising at least one air temperature sensor (ATS) arranged to measure air temperature inside said electrical closed cabinet (ECB).

11. The ozone generating machine (OGM) according to claim 1, further comprising at least one liquid temperature sensor (LTS) arranged to measure liquid temperature inside the closed loop cooling liquid circuit (CLC).

12. The ozone generating machine (OGM) according to claim 1, further comprising:
  at least one liquid temperature sensor (LTS) arranged to measure a liquid temperature inside the closed loop cooling liquid circuit (CLC) and arranged upstream the electric current converter (ECV),
  at least one flow switch arranged to detect liquid flow inside the closed loop cooling liquid circuit (CLC),
  in order to monitor that said electric current converter (ECV) is cooled.

13. The ozone generating machine (OGM) according to claim 1, further comprising at least one liquid pressure sensor arranged to measure liquid pressure inside the closed loop cooling liquid circuit (CLC).

14. The ozone generating machine (OGM) according to claim 1, further comprising a liquid circulation pump (CRP) connected to the closed loop cooling liquid circuit (CLC).

15. Ship (S) comprising an ozone generating machine (OGM) according to any one of the preceding claims.

* * * * *